US009071776B2

(12) United States Patent
Oda et al.

(10) Patent No.: US 9,071,776 B2
(45) Date of Patent: Jun. 30, 2015

(54) REFLECTIVE IMAGING DEVICE AND IMAGE ACQUISITION METHOD

(75) Inventors: Naoki Oda, Tokyo (JP); Yuichi Ogawa, Kyoto (JP); Iwao Hosako, Toyko (JP); Norihiko Sekine, Tokyo (JP)

(73) Assignees: NEC CORPORATION, Tokyo (JP); NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 393 days.

(21) Appl. No.: 13/701,701

(22) PCT Filed: May 20, 2011

(86) PCT No.: PCT/JP2011/062143
§ 371 (c)(1),
(2), (4) Date: Dec. 3, 2012

(87) PCT Pub. No.: WO2011/152285
PCT Pub. Date: Dec. 8, 2011

(65) Prior Publication Data
US 2013/0076912 A1 Mar. 28, 2013

(30) Foreign Application Priority Data

Jun. 4, 2010 (JP) ................................. 2010-128416

(51) Int. Cl.
H04N 5/33 (2006.01)
G01N 21/3581 (2014.01)

(52) U.S. Cl.
CPC ............. *H04N 5/33* (2013.01); *G01N 21/3581* (2013.01)

(58) Field of Classification Search
USPC .................................................. 348/162–168
See application file for complete search history.

(56) References Cited

U.S. PATENT DOCUMENTS 5,623,145 A 4/1997 Nuss
7,735,945 B1 * 6/2010 Sliwa et al. ....................... 347/6
8,284,102 B2 * 10/2012 Hayes et al. .................. 342/374
2007/0003012 A1 1/2007 Taguchi et al.

FOREIGN PATENT DOCUMENTS

JP 8-320254 A 12/1996
JP 2007-010455 A 1/2007
WO 2010/044193 A1 4/2010

OTHER PUBLICATIONS

Yuichi Ogawa, et al., "Interference terahertz label-free imaging for protein detection on a membrane", Optics Express, Dec. 22, 2008, pp. 22083-22089, vol. 16, No. 26.

* cited by examiner

*Primary Examiner* — Nigar Chowdhury
(74) *Attorney, Agent, or Firm* — Sughrue Mion, PLLC

(57) ABSTRACT

In order to generate a two-dimensional image of a sample in a short time using THz waves, provided is a reflective imaging device including a sample holder, a THz wave light source, a THz wave camera, a rotation mechanism for rotating the holder and the camera, and a processing unit. A sample unit includes an incidence member, a sample, and a reflection member. The sample includes a first region of only a membrane and a second region including a biopolymer. The camera detects, with regard to respective incident angles, a THz wave in which interference occurs between a component reflected at an interface between the incidence member and the sample and a component reflected at an interface between the sample and the reflection member, of each portion of the sample unit, and outputs a signal. The processing unit specifies an incident angle at which a signal of a first THz wave that interferes in the first region is relatively small and a signal of a second THz that interferes in the second region is relatively large, and generates a two-dimensional image of the sample based on the signal from the camera with regard to the specified incident angle.

10 Claims, 16 Drawing Sheets

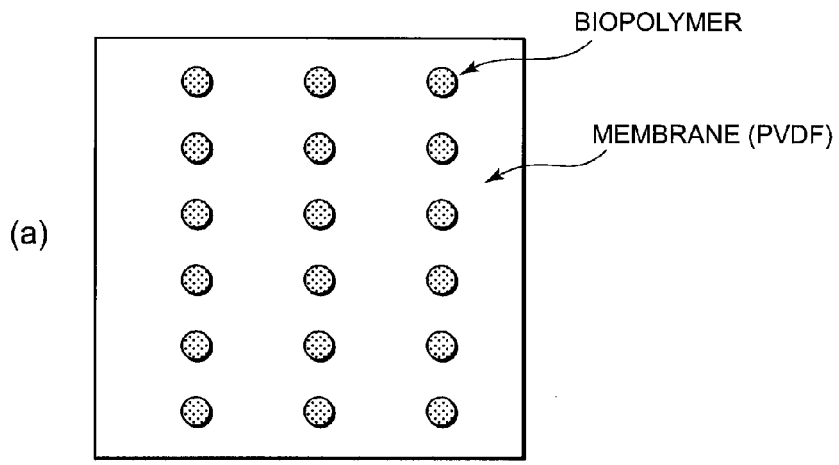
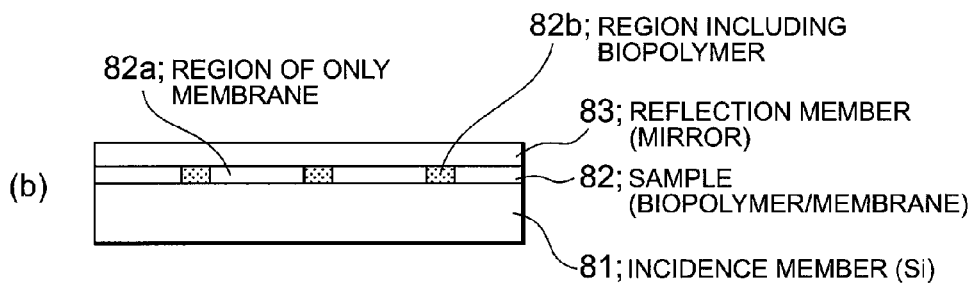
FIG. 4

WHEN Membrane IS 90 μm THICK

| | AT THE CENTER OF FIELD OF VIEW (0°) | AT ONE END OF FIELD OF VIEW (−5.75°) | AT THE OTHER END OF FIELD OF VIEW (+5.75°) |
|---|---|---|---|
| PROTEIN (CONSTRUCTIVE INTERFERENCE) | m'=2, θ'=63°<br>AT THIS TIME, DESTRUCTIVE INTERFERENCE SIDE<br>m=0.99 | | |
| Membrane (DESTRUCTIVE INTERFERENCE) | m=1, θ=62.5°<br>AT THIS TIME, CONSTRUCTIVE INTERFERENCE SIDE<br>m'=2.01 | | |
| COMPROMISE | θ=63°<br>m'=2, m=0.99 | θ=57.25°<br>m'=2.08, m=1.09 | θ=68.75°<br>m'=1.94, m=1.04 |

FIG. 12

WHEN Membrane IS 150 μm THICK

| | AT THE CENTER OF FIELD OF VIEW (0°) | AT ONE END OF FIELD OF VIEW (−5.75°) | AT THE OTHER END OF FIELD OF VIEW (+5.75°) |
|---|---|---|---|
| PROTEIN (CONSTRUCTIVE INTERFERENCE) | m'=4, θ'=32.5° AT THIS TIME, DESTRUCTIVE INTERFERENCE SIDE m=2.82 | | |
| Membrane (DESTRUCTIVE INTERFERENCE) | m=3, θ'=23.5° AT THIS TIME, CONSTRUCTIVE INTERFERENCE SIDE m'=4.15 | | |
| COMPROMISE | θ=28° m'=4.08, m=2.92 | θ=22.25° m'=4.17, m=3.02 | θ=33.75° m'=3.97, m=2.79 |

FIG. 15

REFLECTIVE IMAGING DEVICE AND IMAGE ACQUISITION METHOD

TECHNICAL FIELD

This invention relates to a reflective imaging device and an image acquisition method, and more particularly, to a reflective imaging device and an image acquisition method for generating a two-dimensional image for detecting a biopolymer such as a protein.

BACKGROUND ART

For the purpose of developing an antibody drug, specifying a substance that causes an allergy, and the like, a protein is detected using fluorescent immunoassay, plasmon resonance, optical interference, and the like. In recent years, a method of detecting a protein using terahertz (hereinafter referred to as THz) waves has been proposed.

For example, when THz waves of different wavelengths are applied to a sample, THz waves of specified wavelengths are absorbed due to electromagnetic wave absorption by the sample, and the transmittance-frequency characteristics of the THz waves appear as a waveform specific to the physical properties of the sample. Therefore, by measuring the transmittance of the THz waves, a protein may be detected.

As a method of measuring transmittance of THz waves, THz time-domain spectroscopy (hereinafter referred to as THz-TDS) is known. In this THz-TDS, THz waves emitted from a THz wave generator are collected and applied onto a sample, and after that, THz waves which pass through the sample or THz waves which are reflected by the sample are collected onto a THz detector to be detected. FIG. 18 illustrates an imaging system formed of a THz-TDS system having a near-infrared femtosecond pulse laser 101 as a pump source.

A near-infrared femtosecond pulse laser emitted from the laser 101 for pumping is split by a beam splitter 102, and THz wave pulses are generated from a THz pulse generation side antenna 103 to which bias voltage 104 is applied. Generated THz waves 106 are collected by a paraboloidal mirror 105 to enter a sample unit 107. The incoming THz waves 106 enter a membrane sample 107b which is sandwiched between a high specific resistivity silicon 107a and a reflecting mirror 107c. The THz waves which pass through the membrane sample 107b are reflected by the reflecting mirror 107c. The sample unit 107 is fixed to an XY stage 108. Scanning in an X direction and in a Y direction enables acquirement of a two-dimensional image of the membrane sample 107b.

In this case, as illustrated in FIG. 19, in the sample unit 107, reflection of the incoming THz wave pulses 106 is caused on a lower surface of the high specific resistivity silicon 107a (109a). Then, reflection is caused at an interface between the sample 107b and the high specific resistivity silicon 107a (109b). Further, a component which passes through the sample 107b is reflected by the reflecting mirror 107c (109c). A part of the component which is reflected by the reflecting mirror 107c is reflected again by an upper surface of the high specific resistivity silicon 107a, and, after passing through the sample 107b again, is reflected by the reflecting mirror 107c (109d). These reflected waves 109 are collected by a THz wave receiving side antenna 110 to be detected.

In THz-TDS, for the purpose of acquiring a frequency spectrum by Fourier transform of a waveform of THz wave pulses, a current value at the instant at which THz waves that have passed through a time delay 111 reach the THz pulse receiving side antenna 110 is measured with an ammeter 112 and is recorded in a computer 113.

The above-mentioned membrane sample 107b realizes detection of a trace quantity of a biopolymer on a membrane filter which is a polymeric porous film. The membrane filter is permeable in the THz band, and is made of a material having a low refractive index because of the porosity. Therefore, when a trace quantity of a biopolymer attaches onto the membrane filter, the refractive index of that area is changed.

FIG. 20 shows frequency spectra acquired by Fourier transform of a temporal waveform acquired using the above-mentioned system. As shown in FIG. 20, even when only a trace quantity of streptavidin is coupled on the membrane filter, a frequency is observed at which a large change in transmittance is acquired by a shift of an interference waveform. By forming a two-dimensional image of data sliced at that frequency, the trace quantity of sample may be detected with high sensitivity. FIG. 21 illustrates an exemplary two-dimensional image generated in this way.

PRIOR ART DOCUMENT

Non Patent Literature 1: Yuichi Ogawa et al., OPTICS EXPRESS Vol. 16, No. 26 (2008)

SUMMARY OF THE INVENTION

Problem to be Solved by the Invention

However, in the above-mentioned method, the sample is moved by the XY stage 108, the THz wave pulse waveforms are detected with respect to the respective points on the sample, the frequency spectrum is determined by Fourier transform, the frequency spectrum is analyzed to specify a frequency at which a large change in transmittance is acquired, and an image of data sliced at that frequency is formed. Because such processing is carried out, there is a problem that an enormous amount of time (for example, about eight hours) is necessary for generating a two-dimensional image as illustrated in FIG. 21.

This invention has been made in view of the above-mentioned problem, and a principal object of this invention is to provide a reflective imaging device and an image acquisition method which may generate a two-dimensional image of a sample in a very short time compared with the conventional method using THz waves.

Means to Solve the Problem

In order to achieve the above-mentioned object, according to this invention, there is provided a reflective imaging device, including: a holder for holding a sample unit; an optical system for causing a terahertz wave to enter an entire surface of the sample unit; a camera including a two-dimensional array sensor for detecting the terahertz wave reflected by each portion of the sample unit; a rotation mechanism for rotating the holder to change, in a predetermined angle range, an incident angle of the terahertz wave which enters the sample unit and for rotating the camera so that the terahertz wave reflected by the sample unit is collected to the camera; and a processing unit for processing a signal output from the camera, in which: the sample unit includes, from an incident side of the terahertz wave: an incidence member which transmits the terahertz wave; a sample; and a reflection member which reflects a terahertz wave; the sample includes: a first region of only a membrane having a predetermined refractive index; and a second region including a target substance in the membrane, the target substance having a refractive index which is different from the predetermined refractive index of the membrane; the camera detects a terahertz wave in which interference occurs between a component reflected at an interface between the incidence member and the sample of the sample unit and a component reflected at an interface between the sample and the reflection member of the sample unit, with regard to respective incident angles in the predetermined angle range, and outputs a signal in accordance with a strength of the detected terahertz wave; and the processing unit specifies an incident angle at which a signal of a first terahertz wave that interferes in the first region is relatively small and a signal of a second terahertz wave that interferes in the second region is relatively large, and generates a two-dimensional image of the sample based on the signal output by the camera after the detection with regard to the specified incident angle.

In addition, according to this invention, there is provided an image acquisition method using a reflective imaging device, the image acquisition method including: causing a terahertz wave to enter, at incident angles in a predetermined angle range, an entire surface of a sample unit, the sample unit including, from an incident side of the terahertz wave, an incidence member which transmits the terahertz wave, a sample, and a reflection member which reflects the terahertz wave, the sample including a first region of only a membrane having a predetermined refractive index and a second region including a target substance in the membrane, the target substance having a refractive index which is different from the predetermined refractive index of the membrane; detecting, using a camera including a two-dimensional array sensor, a terahertz wave in which interference occurs between a component reflected at an interface between the incidence member and the sample of the sample unit and a component reflected at an interface between the sample and the reflection member of the sample unit, with regard to the respective incident angles in the predetermined angle range, and outputting a signal in accordance with a strength of the detected terahertz wave; specifying, based on the signal output by the camera after the detection, an incident angle at which a signal of a first terahertz wave that interferes in the first region is relatively small and a signal of a second terahertz wave that interferes in the second region is relatively large; and generating, based on the signal output by the camera after the detection with regard to the specified incident angle, a two-dimensional image of the sample.

Effect of the Invention

According to the reflective imaging device and the image acquisition method of this invention, it is possible to generate a two-dimensional image of the sample in a very short time (for example, several minutes) compared with the conventional method using THz waves.

The reason is that THz waves are applied to the entire surface of the sample under a state in which the incident angle is changed, THz waves which interfere in the region of only the membrane and in the region including the biopolymer, respectively, are detected with the two-dimensional THz wave camera, an incident angle is specified at which destructive interference occurs in the region of only the membrane and constructive interference occurs in the region including the biopolymer, and data detected at the incident angle is used to generate the two-dimensional image of the sample.

BRIEF DESCRIPTION OF THE DRAWING

FIG. 4 illustrate a structure of the sample unit used in the reflective imaging device according to the embodiment of this invention.

FIG. 12 is a table showing the incident angle and the order at the center and at both ends of a field of view in the membrane (PVDF) having a thickness of 90 μm.

FIG. 15 is a table showing the incident angle and the order at the center and at both ends of a field of view in the membrane (PVDF) having a thickness of 150 μm.

MODE FOR EMBODYING THE INVENTION

As described in Background Art, by measuring the transmittance of THz waves, a biopolymer such as a protein may be detected, but in a conventional method, a sample is scanned in an X direction and in a Y direction to acquire a two-dimensional image, and thus, there has been a problem that an enormous amount of time is necessary for the measurement.

Therefore, according to an exemplary embodiment of this invention, in a system including a THz wave light source, a sample rotation mechanism, a THz wave camera, a camera rotation mechanism, and a processing unit, these rotation mechanisms are used to find an incident angle which realizes an interference effect in a sample, that is, constructive interference with respect to a substance having a certain refractive index (for example, a protein) and destructive interference with respect to a substance having another refractive index (for example, a membrane) in the sample, and data detected at the incident angle is used to generate a THz image of the entire sample.

More specifically, while, in the related art, THz wave pulse waves are applied to a sample at a certain incident angle, the reflected waves are received by an antenna, the received signals are Fourier transformed to determine a frequency spectrum, and a frequency at which a large change in transmittance is acquired with respect to a specified substance is specified, according to this embodiment, THz waves are applied to the entire surface of the sample under a state in which the incident angle is changed, THz waves which interfere in a region of only a membrane and in a region including a biopolymer, respectively, are detected with the THz wave camera, and an incident angle is specified at which destructive interference occurs in the region of only the membrane and constructive interference occurs in the region including the biopolymer.

Further, while, in the related art, THz wave pulse waves are applied to a part of the sample and scanning is carried out using an XY stage to generate a two-dimensional sample image, according to this invention, THz waves are applied to the entire sample and the interference waves are imaged with a two-dimensional THz wave camera, thereby generating a two-dimensional sample image.

In this way, the technique used in this embodiment is entirely different from that used in the related art. By using the technique of this embodiment, a two-dimensional image of a sample may be generated in a very short time (several minutes).

Exemplary Embodiments

Figure 1:
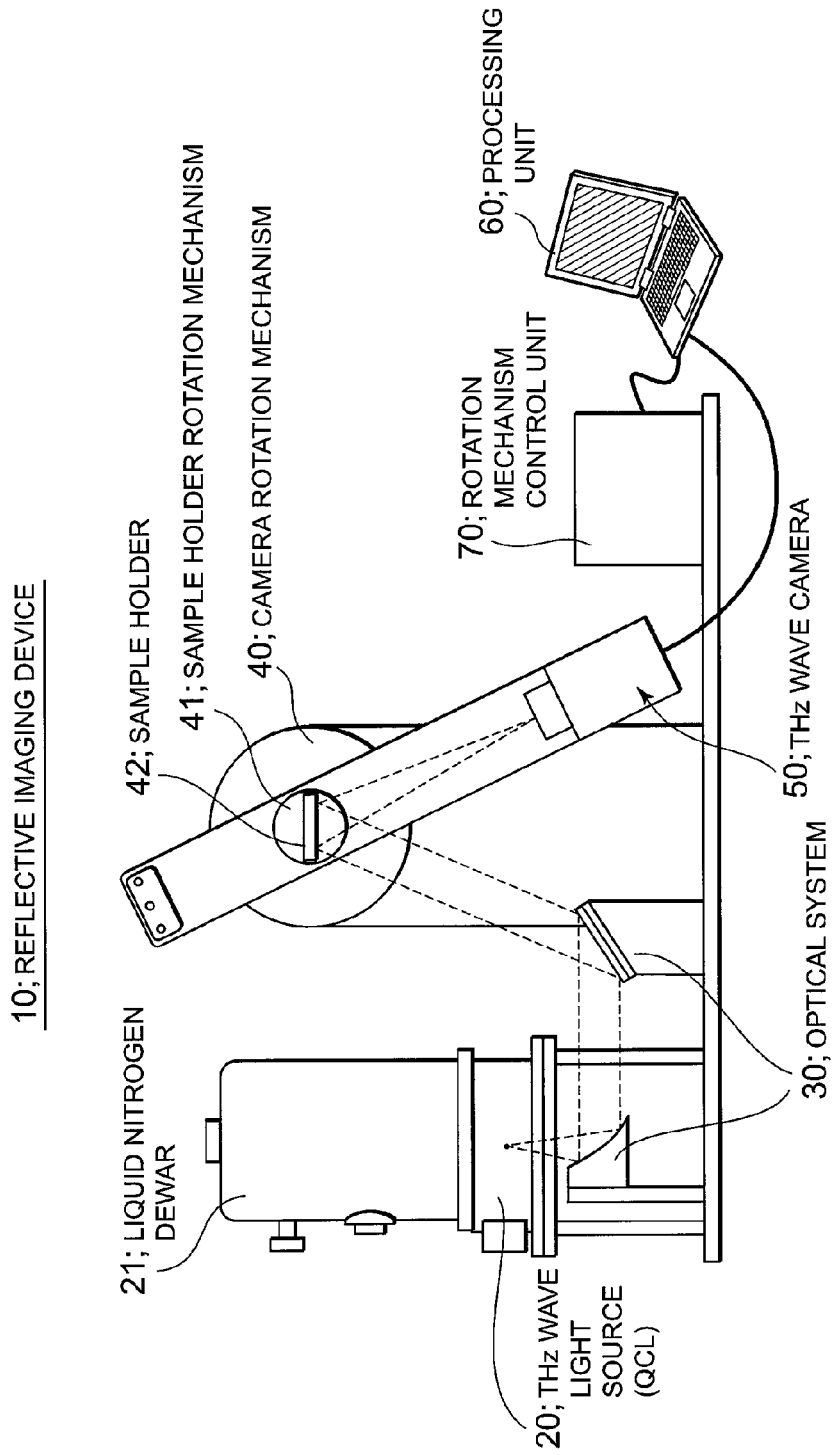
FIG. 1 is a schematic view of a structure of a reflective imaging device according to an exemplary embodiment of this invention.
Figure 2:
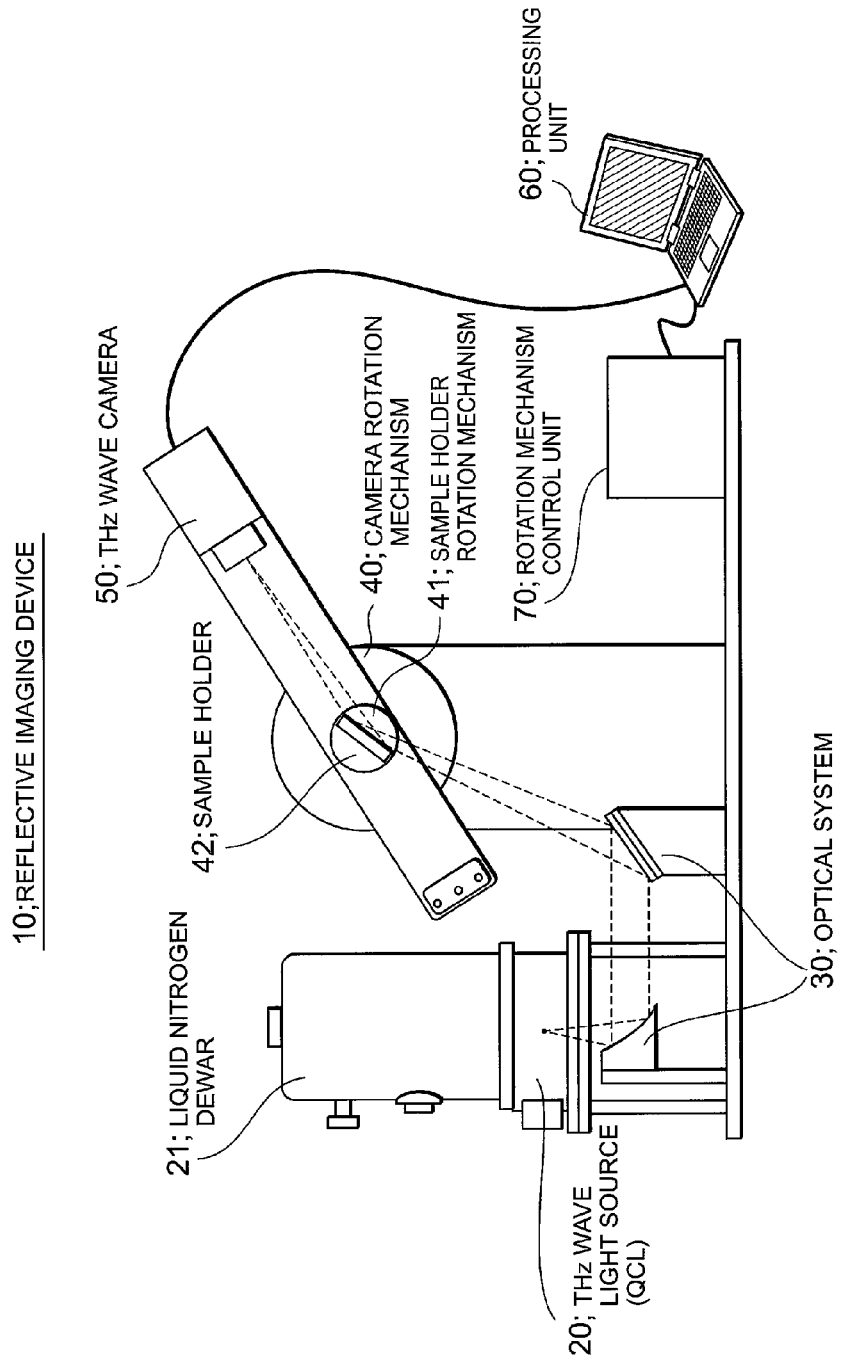
FIG. 2 is a schematic view of a structure of the reflective imaging device according to the embodiment of this invention, and illustrates an arrangement in which the incident angle to a sample holder is larger.
Figure 3:
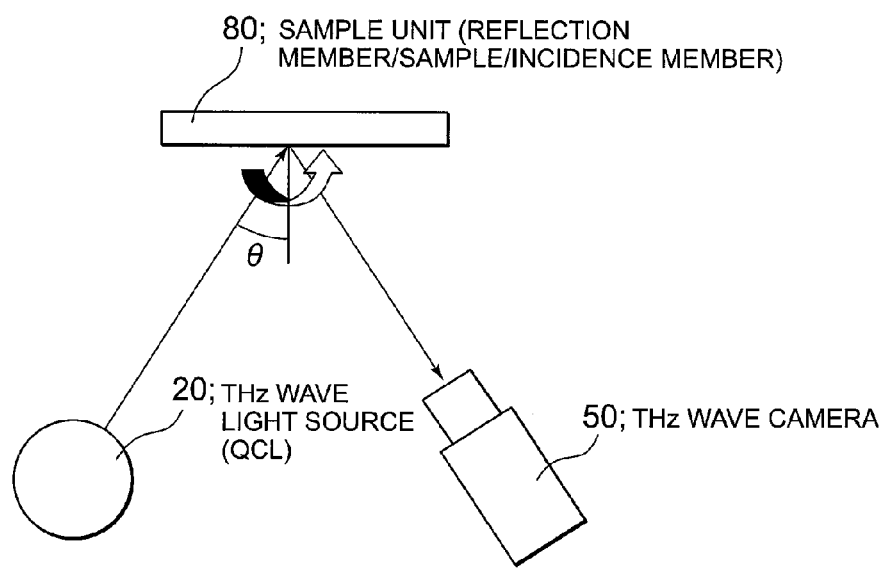
FIG. 3 illustrates the positional relationship among a THz wave light source, a sample unit, and a THz wave camera in the reflective imaging device according to the embodiment of this invention.
Figure 5:
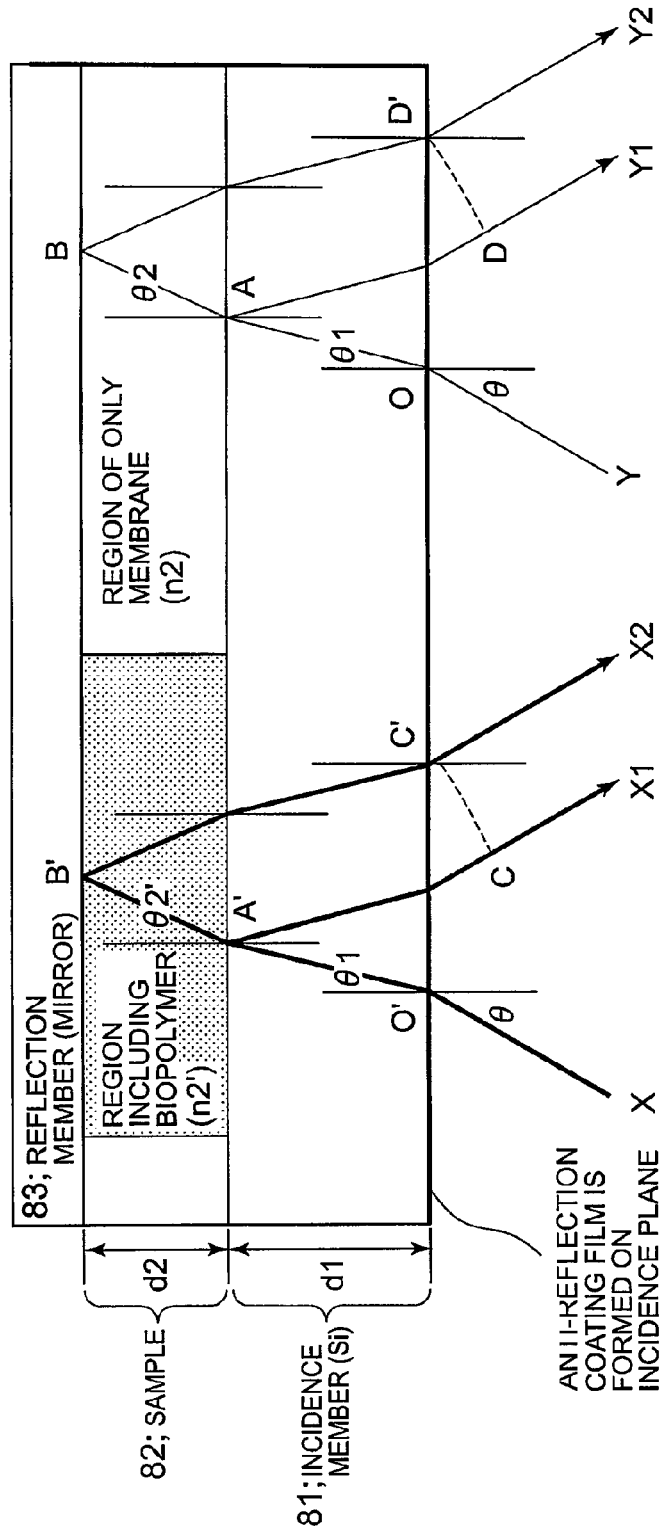
FIG. 5 illustrates optical paths of THz waves which enter the sample unit.
Figure 6:
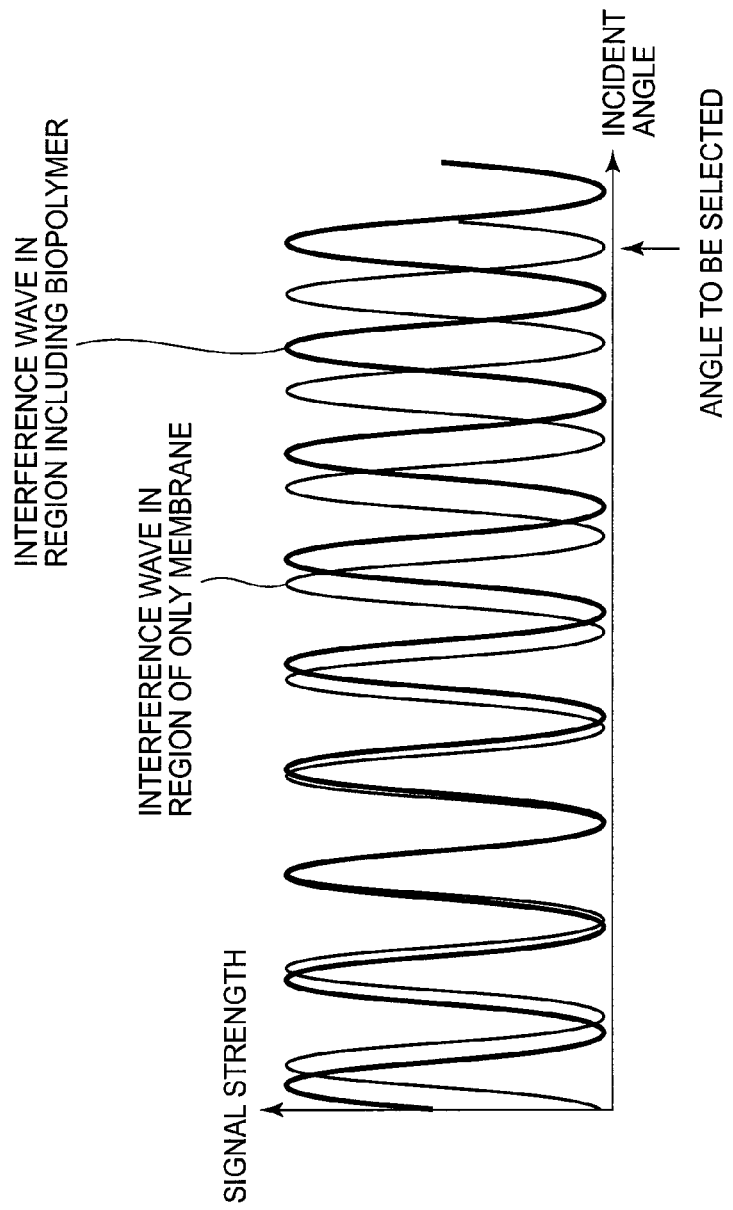
FIG. 6 is a graph showing interference waveforms of signals detected with the THz wave camera (dependence of signal strength on the incident angle).
Figure 7:
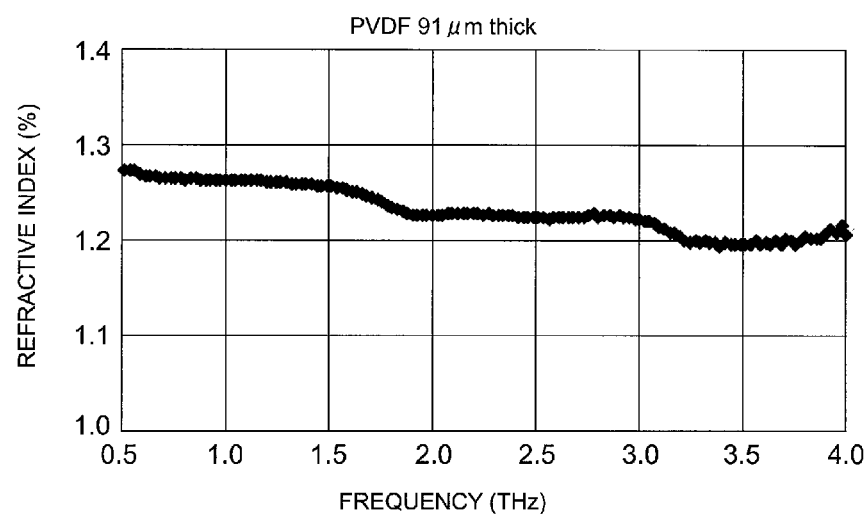
FIG. 7 is a graph showing the dependence of the refractive index of a membrane (PVDF) on the frequency.
Figure 8:
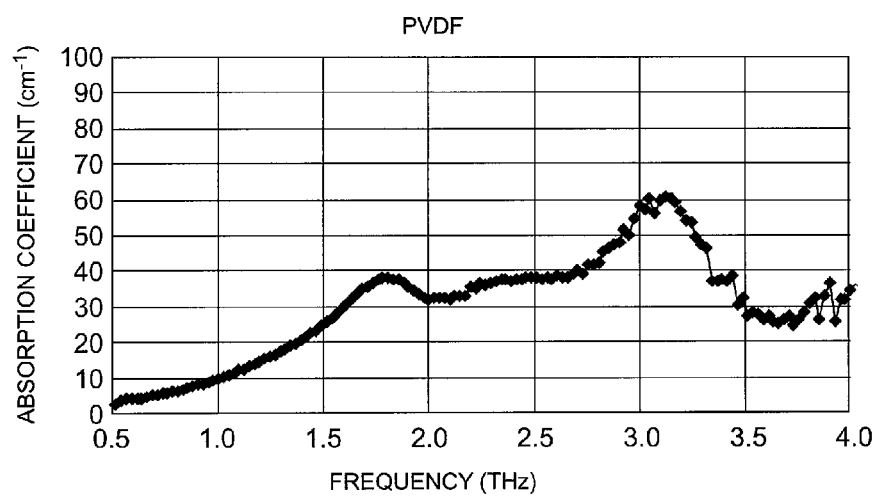
FIG. 8 is a graph showing the dependence of the absorption coefficient of the membrane (PVDF) on the frequency.
Figure 16:
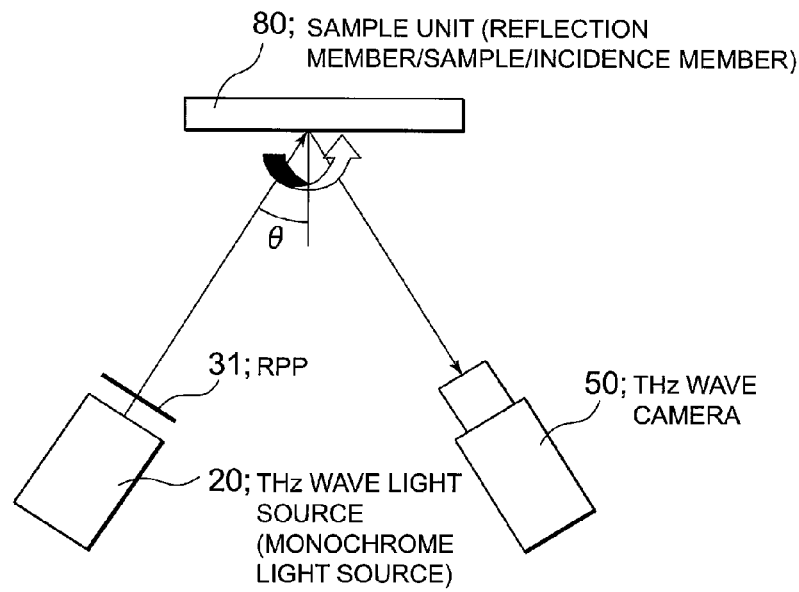
FIG. 16 illustrates another structure of the reflective imaging device according to an embodiment of this invention.
Figure 17:
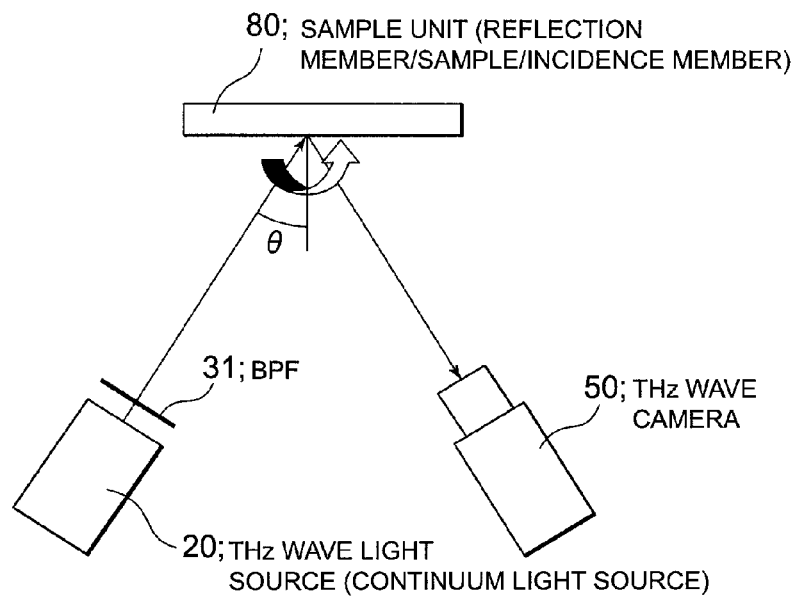
FIG. 17 illustrates still another structure of the reflective imaging device according to an embodiment of this invention.
Figure 18:
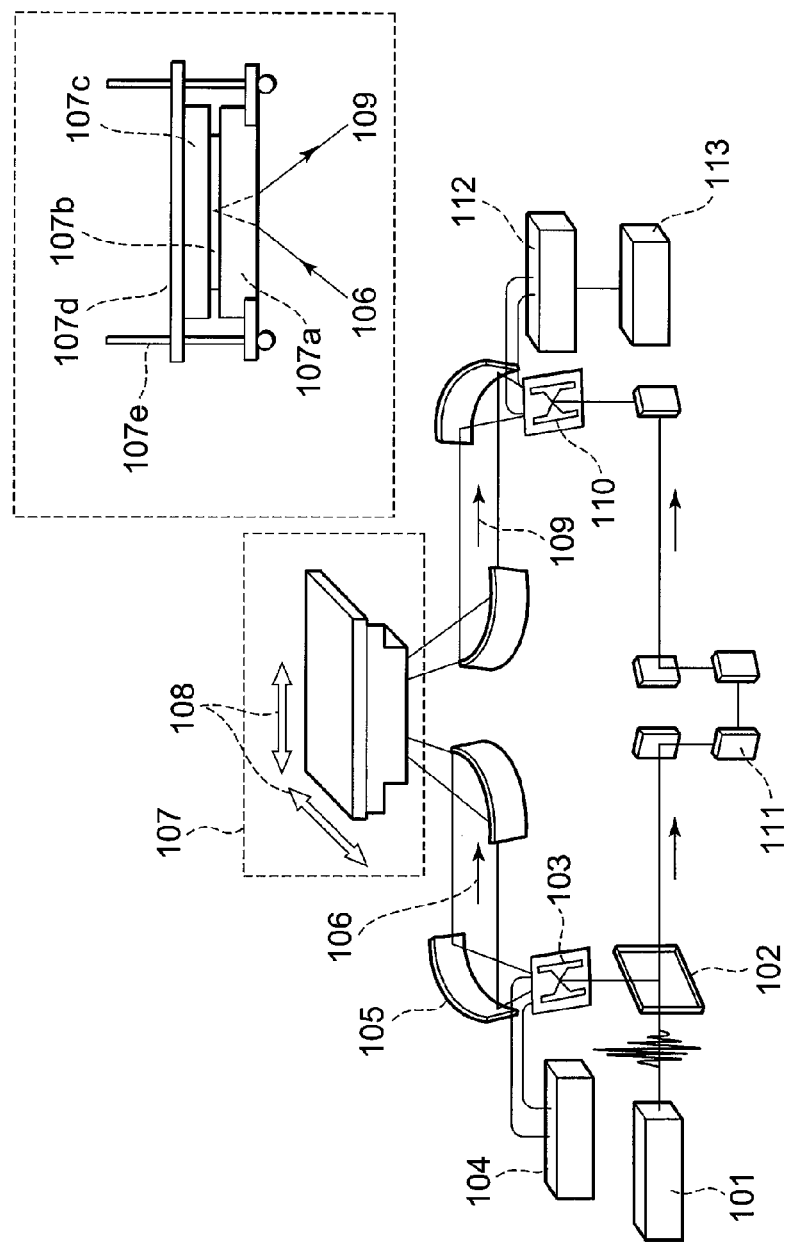
FIG. 18 is a schematic view of a structure of a conventional reflective imaging device.
Figure 19:
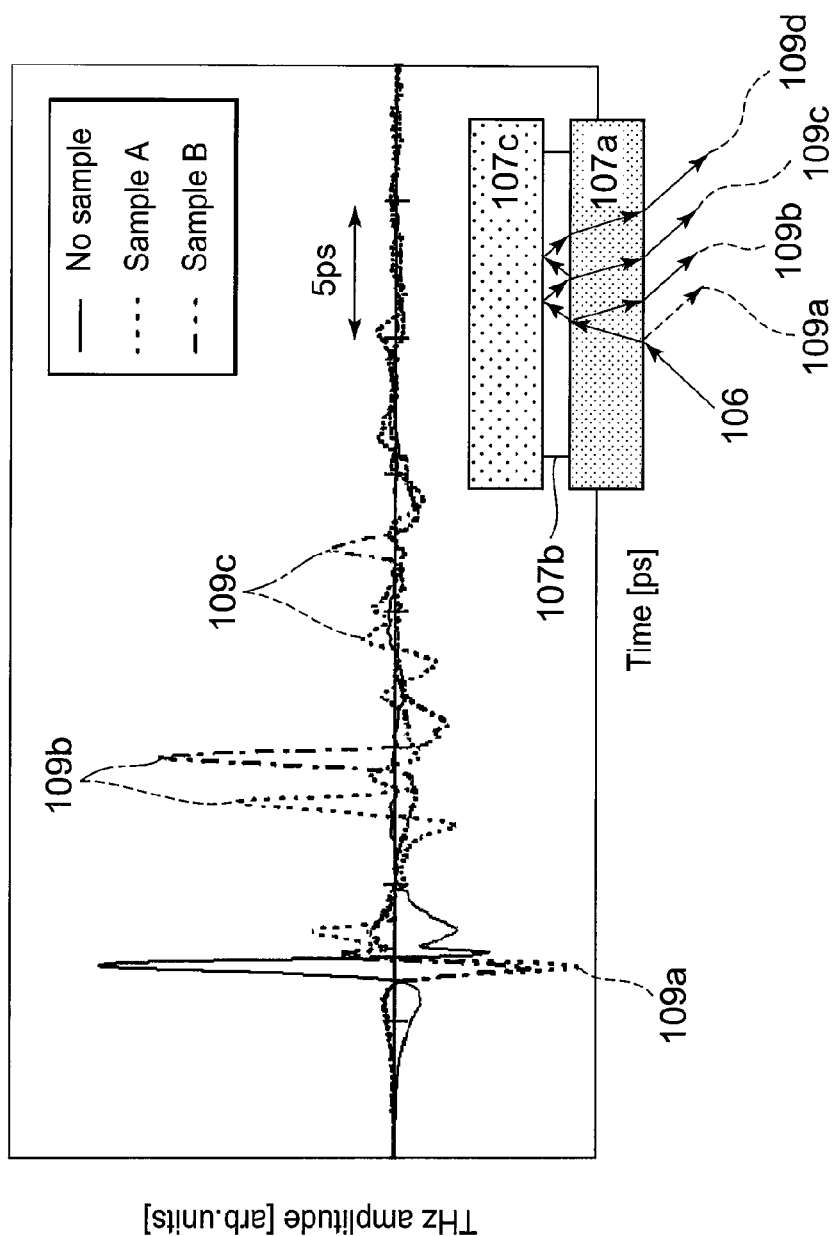
FIG. 19 illustrates signals and optical paths of THz waves which enter a sample unit.
Figure 20:
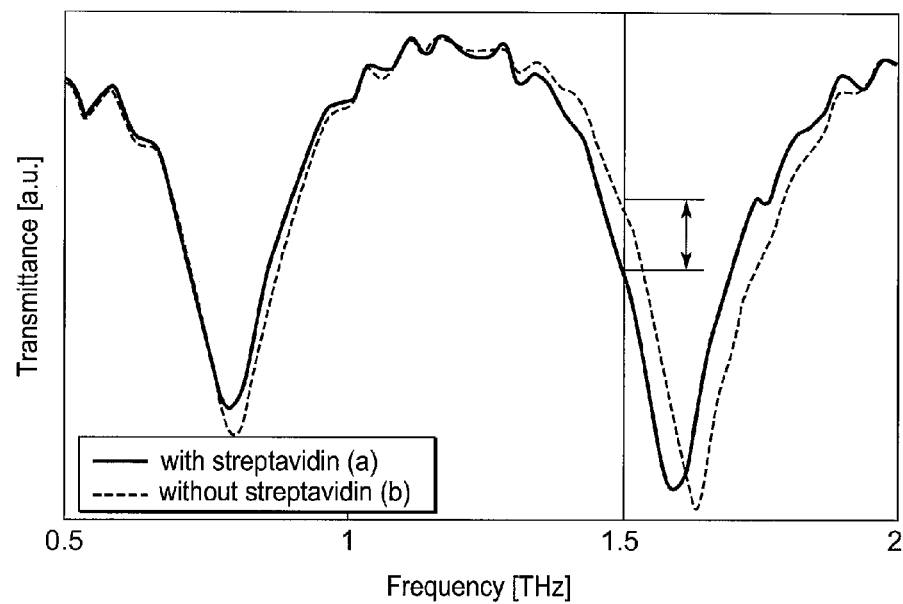
FIG. 20 is a graph showing frequency spectra determined using the conventional reflective imaging device.

In order to describe in further detail the embodiments of this invention described above, reflective imaging devices according to embodiments of this invention are described with reference to FIG. 1 to FIG. 17. FIG. 1 and FIG. 2 are schematic views of a structure of the reflective imaging device according to this invention, and illustrate states in which the incident angle of THz waves is changed. FIG. 3 illustrates the positional relationship among a THz wave light source, a sample unit, and a THz wave camera in the reflective imaging device, and FIG. 4 illustrate a structure of the sample unit. FIG. 5 illustrates optical paths of THz waves which enter the sample unit, and FIG. 6 is a graph showing interference waveforms of THz waves detected with the THz wave camera. FIG. 7 and FIG. 8 are graphs showing characteristics of a membrane (PVDF), FIG. 9 to FIG. 15 illustrate the results of experiments, and FIG. 16 and FIG. 17 illustrate other structures of the reflective imaging device.

As illustrated in FIG. 1 and FIG. 2, a reflective imaging device 10 of this embodiment includes a THz wave light source 20, a liquid nitrogen dewar 21, an optical system 30, a camera rotation mechanism 40, a sample holder rotation mechanism 41, a sample holder 42, a THz wave camera 50, a processing unit 60, a rotation mechanism control unit 70, and the like.

The THz wave light source 20 is a light source for generating electromagnetic waves in a terahertz frequency band between light and radio waves (more specifically, electromagnetic waves having a frequency of 1,012 Hz and a wavelength of approximately from 30 μm to 1 mm), and is, for example, a quantum cascade laser (QCL). When the THz wave light source 20 is required to be cooled using liquid nitrogen or the like, the liquid nitrogen dewar 21 is disposed. Note that, the frequency of the THz waves may be arbitrary insofar as the frequency may be detected with the THz wave camera 50, but, for the purpose of enhancing the detection sensitivity, it is preferred to consider the characteristics of the membrane to be a base material of a sample. For example, when polyvinylidene fluoride (PDVF) is used as the membrane, the refractive index and the absorption coefficient of PDVF exhibit dependence on frequency as shown in FIG. 7 and FIG. 8, and thus, a frequency at which the difference in refractive index from a biopolymer to be detected is large and absorption during propagation is less caused (2.1 to 2.7 THz, 3.5 to 4.4 THz, or the like) may be selected.

The optical system 30 includes a paraboloidal mirror, a minor, and the like for causing THz waves emitted from the THz wave light source 20 to enter the entire surface of the sample as collimated light.

The camera rotation mechanism 40 rotates a rotating body having the THz wave camera 50 at one end thereof and a counterweight at the other end thereof about the sample holder 42 (intermittent rotation by a minute rotation angle or continuous rotation). The sample holder rotation mechanism 41 rotates the sample holder 42 (intermittent rotation by a minute rotation angle or continuous rotation). Further, the sample holder 42 holds the sample unit to be described later. The camera rotation mechanism 40 and the sample holder rotation mechanism 41 operate in synchronization with each other so that, when the sample holder 42 rotates by θ, the rotating body rotates by 2θ (that is, so that THz waves reflected by the sample unit always enter the THz wave camera 50).

The THz wave camera 50 includes, for example, an optical system for collecting THz waves reflected by the sample unit, and a THz wave detector for detecting the collected THz waves. The THz wave detector includes, for example, THz wave detection elements in which elements having a bolometer thin film held in a suspended state using beams are two-dimensionally arranged, a drive circuit for driving the THz wave detection elements, and a signal processing circuit for processing the output of the THz wave detection elements and sending the processed output to the processing unit 60.

The processing unit 60 is a computer unit for processing output signals from the THz wave camera 50. More specifically, the processing unit 60 performs the following processing. Output signals of THz waves which interfere in a region of only the membrane and in a region including a biopolymer, respectively, in the sample with regard to the respective incident angles when the sample holder 42 and the THz wave camera 50 are rotated by the sample holder rotation mechanism 41 and the camera rotation mechanism 40 are acquired from the THz wave camera 50. An incident angle at which a large signal is acquired due to constructive interference in the region including a biopolymer and a small signal is acquired due to destructive interference in the region of only the membrane is specified while the angle is changed. Based on output signals with regard to the respective portions of the sample acquired at the specified incident angle, a two-dimensional image of the sample is generated. This processing may be realized by hardware, or may be realized by a program for causing the processing unit 60 to execute the processing.

The rotation mechanism control unit 70 controls the sample holder rotation mechanism 41 to rotate the sample holder 42 in a predetermined angle range, and controls the camera rotation mechanism 40 to rotate the rotating body for holding the THz wave camera 50 in an angle range which is twice as large as the rotation angle of the sample holder. FIG. 1 illustrates a state in which the incident angle is small, while FIG. 2 illustrates a state in which the incident angle is large.

FIG. 3 illustrates the positional relationship among the THz wave light source 20, a sample unit 80 held by the sample holder 42, and the THz wave camera 50. When THz waves enter at an angle θ with respect to the direction of the normal to the sample unit 80, THz waves reflected by the sample unit 80 exit also at the angle θ with respect to the direction of the normal to the sample unit 80. More specifically, the angle formed by the incident light and the outgoing light is twice as large as the angle formed by the incident angle and the direction of the normal to the sample unit 80. Therefore, when the sample unit 80 is rotated by θ1, the rotating body for holding the THz wave camera 50 is rotated by 2×θ1.

Note that, FIG. 1 to FIG. 3 illustrate an exemplary reflective imaging device 10 of this embodiment, and the structure thereof may be appropriately modified insofar as THz waves are caused to enter the sample under a state in which the incident angle is changed and THz waves which interfere in the respective regions of the sample may be detected.

Next, a structure of the sample unit 80 held by the sample holder 42 is described with reference to FIG. 4.

As illustrated in FIG. 4(b), the sample unit 80 includes a sample 82 in which a substance to be inspected (in this example, a biopolymer such as a protein) is partly disposed, an incidence member 81 disposed on a first main surface of the sample 82 (on the THz wave incident side which is a lower side in FIG. 4(b)), and a reflection member 83 (minor) disposed on a second main surface (on an upper side in FIG. 4(b)), and the sample 82 is sandwiched between the incidence member 81 and the reflection member 83. Note that, although not shown in the figures, the sample unit 80 is sandwiched between a holding plate on the incidence member side and a holding plate on the reflection member side each of which has an opening therein. Both of the holding plates are fixed using a screw or the like so that the parallelism between the first main surface and the second main surface of the sample 82 is maintained.

The above-mentioned incidence member 81 is formed of a material which transmits THz waves such as a high specific resistivity silicon (Si) single crystal (specific resistivity: 10 kΩ·cm or more). Si has a constant refractive index in the THz wave band of 3.415 and a small absorption coefficient, and loss of THz waves inside Si may be regarded as almost zero. Note that, an anti-reflection coating film is formed on a surface of the incidence member 81 (THz wave incidence plane) to inhibit reflection of THz waves on the surface of the incidence member 81.

Further, the reflection member 83 is a mirror which has a refractive index larger than that of the sample 82 and reflects almost 100% of THz waves. Other than that, a member having a negative refractive index such as a meta-material may also be used.

Further, the sample 82 is, as illustrated in FIG. 4(a), formed by attaching a biopolymer such as a protein to a region which is a part of a membrane of PVDF or the like. This PVDF is a porous film, and, as shown in FIG. 7, has a refractive index which is as small as about 1.2 to 1.3. It is expected that, by attachment thereto and penetration thereinto (the depth of which is arbitrary) of a biopolymer, the refractive index becomes larger and an effective to-and-fro optical path becomes larger.

Note that, FIG. 4 illustrate an exemplary sample unit 80 of this embodiment, and the shapes and the materials of the incidence member 81, the sample 82, and the reflection member 83, the arrangement and the size of the biopolymer in the sample 82, and the like may be appropriately modified.

Next, the propagation paths of THz waves in the sample unit 80 are described with reference to FIG. 5. In the following description, the thickness and the refractive index of the incidence member 81 are represented by d1 and n1, respectively. Further, the thickness of the sample 82 is represented by d2, the refractive index of a region 82a of only the membrane in the sample 82 is represented by n2, and the refractive index of a region 82b including a biopolymer is represented by n2'.

Further, a boundary between the reflection member 83 and the sample 82 is referred to as a first interface, a boundary between the sample 82 and the incidence member 81 is referred to as a second interface, and a boundary between the incidence member 81 and the atmosphere is referred to as a third interface. Further, a reflected wave generated at the first interface is referred to as a first surface reflected wave, and a reflected wave generated at the second interface is referred to as a second surface reflected wave. This embodiment is characterized in that interference of the first surface reflected wave generated at the first interface and the second surface reflected wave generated at the second interface is used to analyze the sample 82. Specific description is in the following.

[THz Wave Entering Region 82b Including Biopolymer]

THz waves which enter from the outside of the incidence member 81 (point X) at the incident angle θ pass through the third interface at a point O', and propagate through the incidence member 81 at a first angle (θ1). This first angle is determined by the difference in permittivity between the atmosphere and the incidence member 81. A part of waves propagating through the incidence member 81 enter at a point A' the region 82b including a biopolymer in the sample 82, and a part of the remainder are reflected by the second interface to be reflected waves. The reflected waves pass through the third interface to be emitted to a point X1 via a point C.

On the other hand, propagating waves which enter the region 82b including a biopolymer propagate in the region at a second angle (θ2'). The second angle is determined by the difference in permittivity between the incidence member 81 and the region 82b including a biopolymer. The waves propagating in the region 82b including a biopolymer are reflected by the first interface at a point B' to be reflected waves. A part of the reflected waves are reflected by the second interface, and a part of the remainder pass through the second interface and a point C' of the third interface to be emitted to a point X2.

[THz Wave Entering Region 82a of only Membrane]

THz waves which enter from the outside of the incidence member 81 (point Y) at the incident angle θ pass through the third interface at a point O, and, similarly to the above-mentioned case, propagate through the incidence member 81 at the first angle (θ1). A part of waves propagating through the incidence member 81 enter at a point A the region 82a of only the membrane in the sample 82, and a part of the remainder are reflected by the second interface to be reflected waves. The reflected waves pass through the third interface to be emitted to a point Y1 via a point D.

On the other hand, propagating waves which enter the region 82a of only the membrane propagate in the region at a third angle (θ2). The third angle is determined by the difference in permittivity between the incidence member 81 and the region 82a of only the membrane. The waves propagating in the region 82a of only the membrane are reflected by the first interface at a point B to be reflected waves. A part of the reflected waves are reflected by the second interface, and a part of the remainder pass through the second interface and a point D' of the third interface to be emitted to a point Y2.

In this case, the lengths of respective optical paths X-X1 and X-X2 of THz waves which enter the region 82b including a biopolymer may be expressed as follows:

optical path length $O'-A'-C=2n1d1/\cos\theta1+2d2\tan\theta2\sin\theta$; and optical path length $O'-A'-B'-C'=2n1d1/\cos\theta1+2n2'd2/\cos\theta2'$.

Thus, optical path length difference$=2n2'd2/\cos\theta2'-2d2\tan\theta2\sin\theta$ (1)

Similarly, the lengths of optical paths Y-Y1 and Y-Y2 of THz waves which enter the region 82a of only the membrane may be expressed as follows:

optical path length $O-A-D=2n1d1/\cos\theta1+2d2\tan\theta2\sin\theta$; and optical path length $O-A-B-D'=2n1d1/\cos\theta1+2n2d2/\cos\theta2$.

Thus, the optical path length difference may be expressed as follows.

optical path length difference$=2n2d2/\cos\theta2-2d2\tan\theta2\sin\theta$ (2)

$\cos\theta2$ and $\tan\theta2$ are uniquely determined by n1 and n2, and $\cos\theta2'$ and $\tan\theta2'$ are uniquely determined by n1 and n2', and thus, the respective optical path length differences are functions of θ. Therefore, when THz waves, which are reflected in the respective regions while the sample unit 80 is rotated by the sample holder rotation mechanism 41 and the THz wave camera 50 is rotated by the camera rotation mechanism 40, are detected, signals in the respective regions are interference waves the strengths of which repeatedly change in accordance with the incident angle.

FIG. 6 shows signal strengths of the THz wave camera 50 under a state in which the incident angle is changed. A signal of THz waves reflected by the region 82b including a biopolymer (thick line) and a signal of THz waves reflected by the region 82a of only the membrane (thin line) are interference waves having different periods in accordance with the difference between n2 and n2'.

Therefore, the processing unit 60 stores in a memory or the like signals output from the THz wave camera 50 at the respective incident angles, and specifies an angle at which a signal of THz waves which interfere in the region 82b including a biopolymer (thick line) is a peak of the interference waves and a signal of THz waves which interfere in the region 82a of only the membrane (thin line) is a valley of the interference waves (for example, the incident angle indicated by an arrow in the figure) while the angle is changed. Note that, when there are a plurality of incident angles which satisfy the above-mentioned conditions, among them, one at which the signal of THz waves that interfere in the region 82b including a biopolymer is the largest may be selected, or one at which the ratio between the two signals is the largest may be selected.

Figure 21:
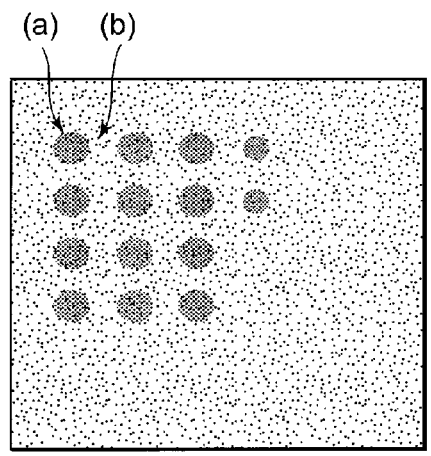
FIG. 21 illustrates an exemplary two-dimensional image acquired using the conventional reflective imaging device.

The processing unit 60 processes signals output from the THz wave camera 50 at the specified incident angle stored in advance in a memory or the like (or, signals output from the THz wave camera 50 at the specified incident angle after the incident angle is specified and the rotation mechanism control unit 70 is controlled to adjust the angles of the sample holder 42 and the THz wave camera 50) to generate a two-dimensional image illustrating a distribution of signal strengths of the respective points of the sample 82 (for example, a two-dimensional image as illustrated in FIG. 21 of the related art).

In this way, by specifying an incident angle at which the signal of THz waves which interfere in the region 82b including a biopolymer is relatively larger with respect to the signal of THz waves which interfere in the region 82a of only the membrane, the signal contrast between the region 82b including a biopolymer and the region 82a of only the membrane may be enhanced, and, even when, for example, the attaching amount of biopolymer is small or the difference in refractive index between the biopolymer and the membrane is small, a region to which the biopolymer attaches may be identified without fail.

Further, in the reflective imaging device 10 of this embodiment, THz waves are applied to the entire sample unit 80 and THz waves which interfere in the respective portions of the sample unit 80 are detected at a time by the THz wave camera 50, and thus, compared with the related art in which a sample is scanned using an XY stage, a two-dimensional image of the sample may be generated far faster.

Figure 9:
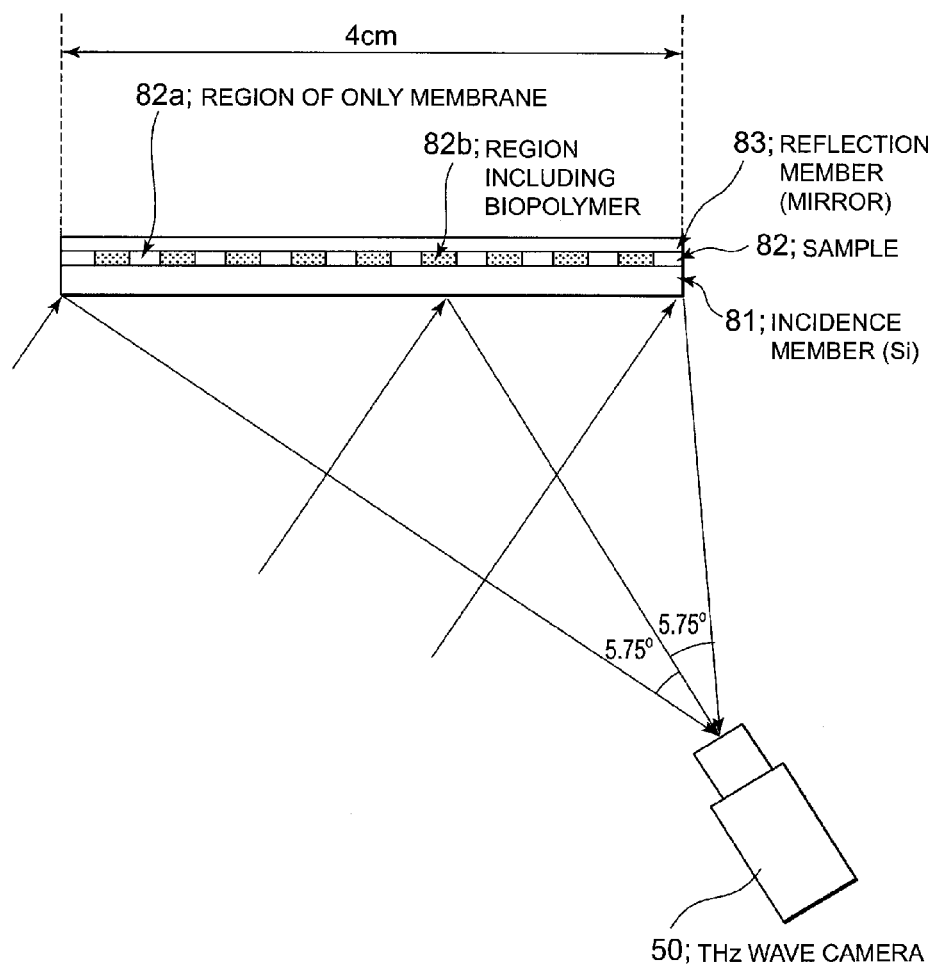
FIG. 9 illustrates a specific example of a sample.

The result of an experiment with regard to the sample 82 using PVDF as the membrane and having a protein as the biopolymer attached thereto is as follows. In this experiment, as illustrated in FIG. 9, the sample unit 80 was sized to be a square of 4 cm×4 cm, and the distance between the sample unit 80 and the THz wave camera 50 is 20 cm. In this case, the angle formed by the THz wave camera 50 and both the ends of the sample 80 is ±5.75°. Further, the frequency of the THz waves is 3.1 THz (97 μm), and, at this frequency, the refractive index of the protein is 1.4 while the refractive index of PVDF is 1.2.

Figure 10:
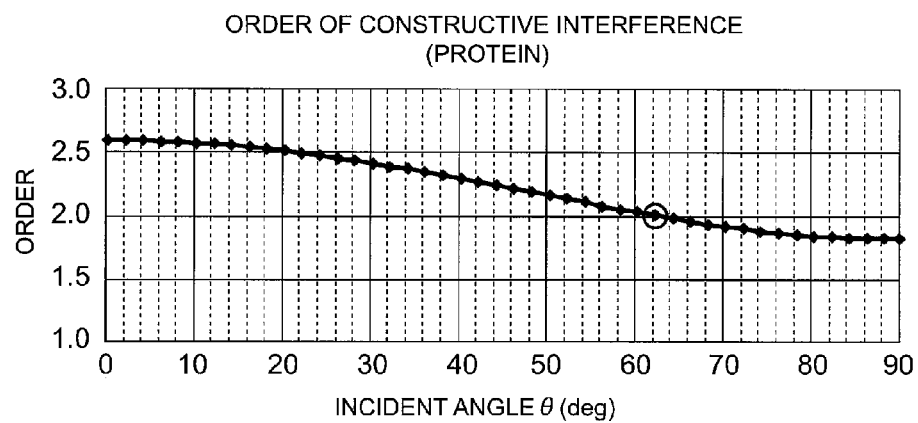
FIG. 10 is a graph showing the order of constructive interference of a protein in the membrane (PVDF) having a thickness of 90 μm.
Figure 11:
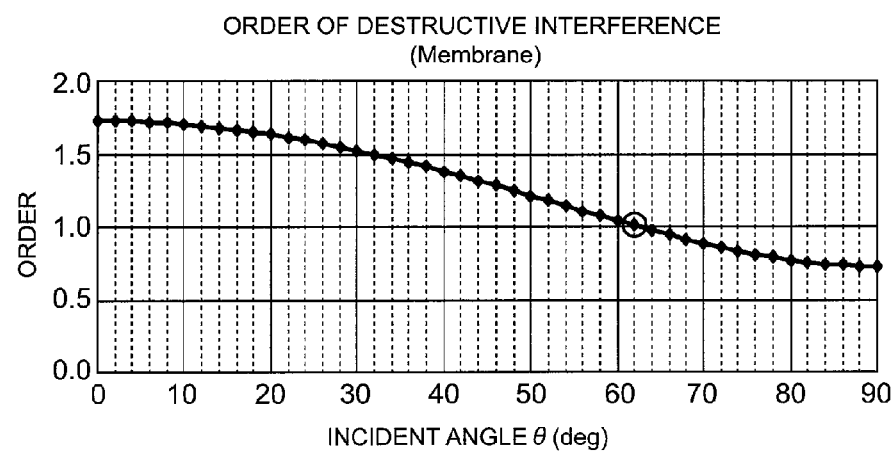
FIG. 11 is a graph showing the order of destructive interference of the membrane (PVDF) having a thickness of 90 μm.

FIG. 10 to FIG. 12 show results when PVDF at a thickness of 90 μm was used. FIG. 10 is a graph showing the dependence on the incident angle of a value determined by dividing the optical path length difference between the optical paths X-X1 and X-X2 in the region including the protein (Eq. 1) by the wavelength of the THz waves (97 μm), and shows that, when the incident angle is 63 degrees, the order of the constructive interference is approximately 2 (the optical path length difference is an even multiple of a half-wavelength of the THz waves). On the other hand, FIG. 11 is a graph showing the dependence on the incident angle of a value determined by subtracting ½ from a quotient of the optical path length difference between the optical paths Y-Y1 and Y-Y2 in the region of only the membrane (Eq. 2) divided by the wavelength of the THz waves (97 μm), and shows that, when the incident angle is 62.5 degrees, the order of the destructive interference is approximately 1 (the optical path length difference is an odd multiple of a half-wavelength of the THz waves).

From FIG. 10 and FIG. 11, when the incident angle is 63 degrees, the interference waves in the region including the protein is a peak and the interference waves in the region of only the membrane is a valley, and the region including the protein may be identified without fail.

Further, FIG. 12 is a table providing a summary of the orders of the constructive interference (m') and the orders of the destructive interference (m) at the center, at one end (incident angle is 63−5.75=57.25 degrees), and at the other end (incident angle is 63+5.75=68.25 degrees) of the sample. From FIG. 12, at the one end, the order of the constructive interference is 2.08, the order of the destructive interference is 1.09, and, at the other end, the order of the constructive interference is 1.94, and the order of the destructive interference is 1.04, which slightly deviate from the values at the center of the sample. However, with deviations at such a level, the region including the protein may be identified, and thus, the incident angle specified with respect to the center may be applied to the entire sample.

Figure 13:
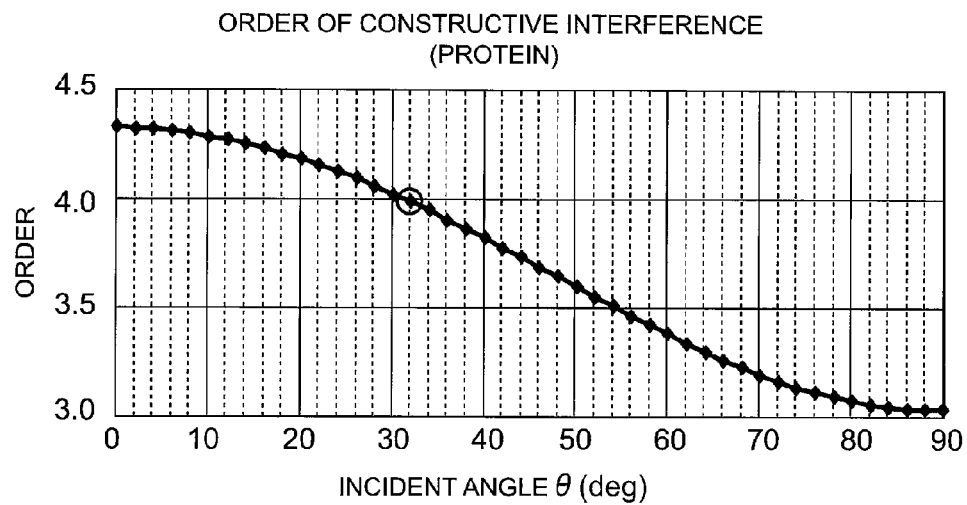
FIG. 13 is a graph showing the order of constructive interference of a protein in the membrane (PVDF) having a thickness of 150 μm.
Figure 14:
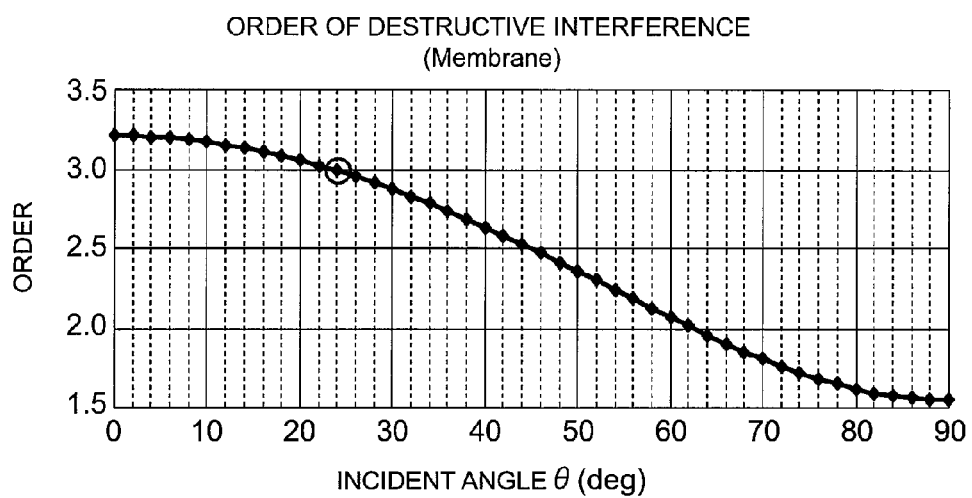
FIG. 14 is a graph showing the order of destructive interference of the membrane (PVDF) in the membrane having a thickness of 150 μm.

FIG. 13 to FIG. 15 show results when PVDF at a thickness of 150 μm was used. FIG. 13 is a graph showing the dependence on the incident angle of a value determined by dividing the optical path length difference between the optical paths X-X1 and X-X2 in the region including the protein (Eq. 1) by the wavelength of the THz waves (97 μm), and shows that, when the incident angle is 32.5 degrees, the order of the constructive interference is approximately 4 (the optical path length difference is an even multiple of a half-wavelength of the THz waves). On the other hand, FIG. 14 is a graph showing the dependence on the incident angle of a value determined by subtracting ½ from a quotient of the optical path length difference between the optical paths Y-Y1 and Y-Y2 in the region of only the membrane (Eq. 2) divided by the wavelength of the THz waves (97 μm), and shows that, when the incident angle is 23.5 degrees, the order of the destructive interference is approximately 3 (the optical path length difference is an odd multiple of a half-wavelength of the THz waves).

From FIG. 13 and FIG. 14, when the incident angle is 28 degrees corresponding to the average between 32.5 degrees and 23.5 degrees, the interference waves in the region including the protein is a peak and the interference waves in the region of only the membrane is a valley, and the region including the protein may be identified without fail.

Further, FIG. 15 is a table providing a summary of the orders of the constructive interference (m') and the orders of the destructive interference (m) at the center, at one end (incident angle is 28−5.75=22.25 degrees), and at the other end (incident angle is 28+5.75=33.75 degrees) of the sample. From FIG. 15, at the one end, the order of the constructive interference is 4.17, the order of the destructive interference is 3.02, and, at the other end, the order of the constructive interference is 3.97, and the order of the destructive interference is 2.79, which deviate larger than the case where PVDF at a thickness of 90 μm is used. In this case, the incident angle specified with respect to the center may be applied to the entire sample, but, for the purpose of identifying the region including the protein more accurately, it is preferred to adjust the thickness of PVDF or to divide the sample into a plurality of regions (a central region and end regions), or to specify optimum incident angles with regard to the respective regions to generate two-dimensional images, and to combine the two-dimensional images of the respective regions to generate a two-dimensional image of the entire sample.

Note that, this invention is not limited to the above-mentioned embodiments and the structure and the control thereof may be appropriately modified within the scope of this invention.

For example, when a monochrome light source having a high coherency such as a quantum cascade laser (QCL) or a backward wave oscillator (BWO) is used as the THz wave light source 20, light applied from the THz wave light source 20 generates an interference pattern to cause a problem when an image is acquired. Accordingly, when such a monochrome light source is used, by inserting a random phase plate (RPP) 31 as illustrated in FIG. 16, the coherency may be eliminated to remove the interference pattern.

Further, when a continuum light source such as a blackbody furnace or a high pressure Hg lamp is used as the THz wave light source 20, by inserting a band-pass filter (BPF) 32 as illustrated in FIG. 17, the coherency may be improved.

Further, in the above-mentioned embodiments, a case in which a biopolymer such as a protein is detected is described, but this invention may be similarly applied to a case in which an arbitrary substance having a refractive index that is different from the refractive index of a base material is detected.

Industrial Applicability

This invention may be used for a system for detecting a region having a different refractive index. In particular, this invention may be used for a system for detecting a region including a biopolymer such as a protein in a sample in which the biopolymer is partly adsorbed to a membrane, and may be used for promptly screening for searching for a candidate substance in the field of drug discovery.

The invention claimed is:

1. A reflective imaging device, comprising:
a light source for generating a terahertz wave;
a holder for holding a sample unit;
an optical system for causing the terahertz wave from the light source to enter an entire surface of the sample unit;
a camera including a two-dimensional array sensor for detecting the terahertz wave reflected by the sample unit;
a rotation mechanism for rotating the holder to change, in a predetermined angle range, an incident angle of the terahertz wave which enters the sample unit and for rotating the camera so that the terahertz wave reflected by the sample unit is collected to the camera; and
a processing unit for processing a signal output from the camera, wherein:
the sample unit comprises, from an incident side of the terahertz wave:
an incidence member which transmits the terahertz wave;
a sample; and
a reflection member which reflects a terahertz wave;
the sample comprises:
a first region of only a membrane having a predetermined refractive index; and
a second region including a target substance in the membrane, the target substance having a refractive index which is different from the predetermined refractive index of the membrane;
the camera detects a terahertz wave in which interference occurs between a component reflected at an interface between the incidence member and the sample of the sample unit and a component reflected at an interface between the sample and the reflection member of the sample unit, with regard to respective incident angles in the predetermined angle range, and outputs a signal in accordance with a strength of the detected terahertz wave; and
the processing unit specifies an incident angle at which a signal of a first terahertz wave that interferes in the first region is relatively small and a signal of a second terahertz wave that interferes in the second region is relatively large, and generates a two-dimensional image of the sample based on the signal output by the camera after the detection with regard to the specified incident angle.

2. A reflective imaging device according to claim 1, wherein, at the specified incident angle, the signal of the first terahertz wave is a valley of an interference waveform and the signal of the second terahertz wave is a peak of an interference waveform.

3. A reflective imaging device according to claim 1, wherein an anti-reflection coating film is formed on a surface of the incidence member on a terahertz wave incident side, and the anti-reflection coating film inhibits reflection of the terahertz wave by the surface of the incidence member.

4. A reflective imaging device according to claim 1, wherein the light source comprises a monochrome light source, and a random phase plate (RPP) is disposed in an optical path of the terahertz wave between the light source and the sample unit.

5. A reflective imaging device according to claim 1, wherein the light source comprises a continuum light source, and a band-pass filter (BPF) is disposed in an optical path of the terahertz wave between the light source and the sample unit.

6. A reflective imaging device according to claim 1, wherein the membrane comprises polyvinylidene fluoride (PDVF) and the target substance comprises a protein.

7. An image acquisition method using a reflective imaging device, the image acquisition method comprising:
  causing a terahertz wave to enter, at incident angles in a predetermined angle range, an entire surface of a sample unit, the sample unit comprising, from an incident side of the terahertz wave, an incidence member which transmits the terahertz wave, a sample, and a reflection member which reflects the terahertz wave, the sample comprising a first region of only a membrane having a predetermined refractive index and a second region including a target substance in the membrane, the target substance having a refractive index which is different from the predetermined refractive index of the membrane;
  detecting, using a camera including a two-dimensional array sensor, a terahertz wave in which interference occurs between a component reflected at an interface between the incidence member and the sample of the sample unit and a component reflected at an interface between the sample and the reflection member of the sample unit, with regard to the respective incident angles in the predetermined angle range, and outputting a signal in accordance with a strength of the detected terahertz wave;
  specifying, based on the signal output by the camera after the detection, an incident angle at which a signal of a first terahertz wave that interferes in the first region is relatively small and a signal of a second terahertz wave that interferes in the second region is relatively large; and
  generating, based on the signal output by the camera after the detection with regard to the specified incident angle, a two-dimensional image of the sample.

8. An image acquisition method according to claim 7, wherein the reflective imaging device comprises:
  a light source for generating the terahertz wave;
  a holder for holding the sample unit;
  an optical system for causing the terahertz wave from the light source to enter the entire surface of the sample unit;
  the camera;
  a rotation mechanism for rotating the holder to change in a predetermined angle range, an incident angle of the terahertz wave which enters the sample unit and for rotating the camera so that the terahertz wave reflected by the sample unit is collected to the camera; and
  a processing unit for processing a signal output from the camera.

9. An image acquisition method according to claim 7, wherein, at the specified incident angle, the signal of the first terahertz wave is a valley of an interference waveform and the signal of the second terahertz wave is a peak of an interference waveform.

10. An image acquisition method according to claim 7, wherein an anti-reflection coating film is formed on a surface of the incidence member of the sample unit on a terahertz wave incident side, and the anti-reflection coating film inhibits reflection of the terahertz wave by the surface of the incidence member.

* * * * *